United States Patent
Brennan et al.

(10) Patent No.: US 9,460,641 B2
(45) Date of Patent: Oct. 4, 2016

(54) WRIST BAND

(71) Applicant: Brenmoor Limited, Cross Hills, Yorkshire (GB)

(72) Inventors: Paul Brennan, Skipton (GB); Michael Moorhouse, Bradford (GB)

(73) Assignee: Brenmoor Limited, Yorkshire (GB)

( * ) Notice: Subject to any disclaimer, the term of this patent is extended or adjusted under 35 U.S.C. 154(b) by 0 days.

(21) Appl. No.: 14/675,794

(22) Filed: Apr. 1, 2015

(65) Prior Publication Data
US 2015/0255007 A1  Sep. 10, 2015

Related U.S. Application Data

(63) Continuation-in-part of application No. 14/053,826, filed on Oct. 15, 2013, now abandoned.

(51) Int. Cl.
*A44C 5/00* (2006.01)
*G09F 3/00* (2006.01)
*A61B 5/117* (2016.01)

(52) U.S. Cl.
CPC .............. *G09F 3/005* (2013.01); *A44C 5/00* (2013.01); *A61B 5/117* (2013.01); *A61B 90/94* (2016.02)

(58) Field of Classification Search
CPC ... A61L 15/58; A61F 13/02; A61F 13/0203; A61F 13/023; A61F 13/0276; A61F 5/0118; A61F 13/107; A61F 5/01; A41D 19/01582; A47B 21/0371; G09F 3/005; B42D 15/00; B42P 2241/22; A44C 5/0015; A61B 19/44
See application file for complete search history.

(56) References Cited

U.S. PATENT DOCUMENTS

| 3,927,669 | A  | * | 12/1975 | Glatt | ................................ 602/47 |
| 7,454,854 | B2 | * | 11/2008 | Riley et al. | ...................... 40/633 |
| 2009/0105625 | A1 | * | 4/2009 | Kohner et al. | ................... 602/54 |
| 2012/0056719 | A1 | * | 3/2012 | Krishna et al. | ............. 340/10.1 |
| 2012/0238933 | A1 | * | 9/2012 | Murphy et al. | ................. 602/53 |

* cited by examiner

*Primary Examiner* — Cassandra Davis
(74) *Attorney, Agent, or Firm* — Thomas E. Sisson PLLC

(57) ABSTRACT

The invention provides for a medical wrist band, specifically for infants and babies, which is economical to manufacture, durable, easy on the skin, does not cause allergic reactions and cannot be removed and reapplied without being damaged.

1 Claim, 1 Drawing Sheet

WRIST BAND

Figure 1:
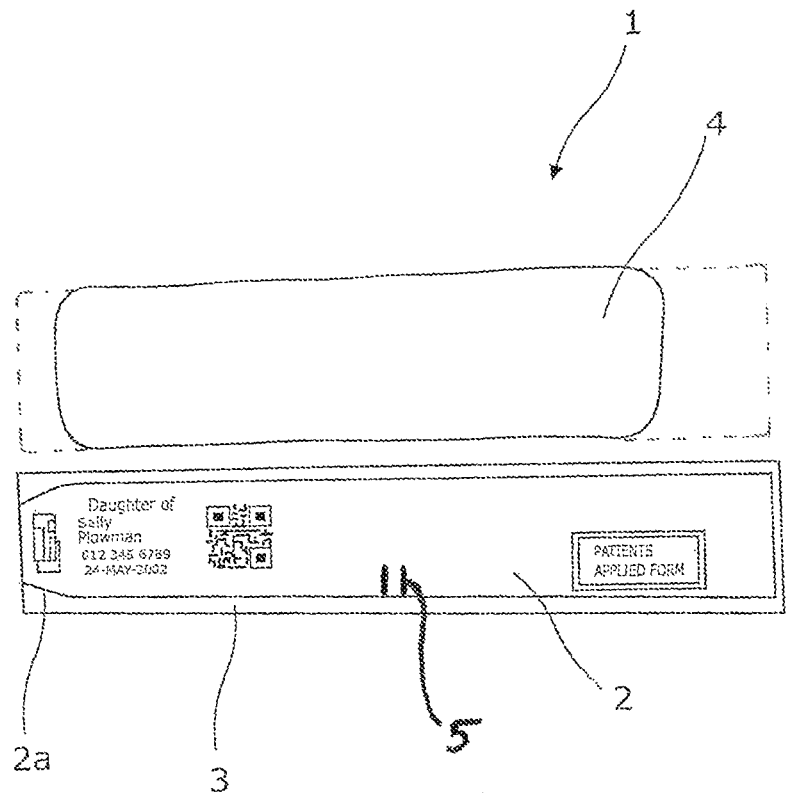

This is a continuation-in-part application claiming priority to co-pending U.S. patent application Ser. No. 14/053,836, filed Oct. 15, 2013, and incorporates the same herein for all purposes

FIELD OF THE INVENTION

This invention relates to wrist bands, such as are nowadays applied to every patient upon admission to hospital.

BACKGROUND OF THE INVENTION

Such wrist bands are well known and normally consist of a thermal, laser or inkjet printable plastic strap which is fastened to the patients' wrists detailing the person's ID and treatments.

The plastic strap is strong enough to survive several weeks of wear and tear on patients' wrists and normally is only replaced after a surgical intervention or other procedure that changes the patient's data.

It has been found, however, that the standard wrist bands are not suitable for infants and babies. The edges of the plastic can rub and cut the baby's skin leading to unnecessary medical complications.

A solution is known from US2006/0218837 A1 (J M Riley). It involves using a band of Velcro™ which can be looped around the infant's wrist and joined with a printable label attached to the outside of the Velcro band. The label has two slots by means of which it can be attached to the tongue which has the hook part of the Velcro on its inside. There is however, a problem with such Velcro strips. By definition, they are easily removable and the printable label can easily be removed from the Velcro band.

Since babies and infants are normally not in a position to offer explanations to staff, wrist band switches are not easily spotted and can lead to mistaken identities with all the consequences of such a mix up. What is more, the "Riley" solution is vulnerable to malicious interference which can go undetected for considerable time. A further factor speaking against the Velcro (Riley) solution is cost.

SUMMARY OF THE INVENTION

The invention provides a wrist band as set out in claim 1. It is directed at remedying the above mentioned problems. It is to create a wrist band which can be used for babies and infants and other patients, is economical to manufacture, durable, easy on the skin, does not cause allergic reactions and, most importantly, cannot be removed and reapplied without the band being damaged or showing signs of tampering.

The band is made from two strips of material, the first strip comprising a latex free inert foam. Preferably the foam strip is fashioned from sheeting of between 2 and 3 mm in thickness. More preferably, the sheeting is of about 1.5 mm thickness and may be any length or width required.

The complete wrist band consists of the first foam section of appropriate length, the particular length depending on the size of the patient, and a second plasticized strip in the form of an elongated label comprising a sticky adhesive back covered by a support layer or backing strip. The label may be preprinted or may be printable on by a printer on demand. The plasticized strip is peeled off its backing strip and attached to the surface of one end of the foam strip. The foam strip is then wrapped around the patient's wrist and the plasticized strip wound over the top onto the foam. The plasticized strip adheres to the foam and overlaps back onto its own surface, such that the ends of the plasticized strip are adhered to one another when wrapped around the foam strip. This forms a continuous loop of the plasticized strip around the patient's wrist or ankle and holds the whole band together, ensuring only the foam strip is in contact with the patient's limb.

Once the foam strip and the plasticized strip are adhered together with the adhesive backing, the two strips resist separation. The adhesive on the plasticized strip is such that it will not peel away from the foam without tearing and showing signs of tampering. There is also the option to add security cuts into the plasticized strip which are designed to tear if the product is tampered with.

The invention has been described by means of the baby example. The extent of the invention covers adult patients as well as infants. It can be used anywhere where allergic reactions are likely that make the use of the standard wrist band unsuitable. Naturally, the band can also be used as ankle bands where appropriate, as with very small babies or patients with thinning and delicate skin due to age or illness.

DESCRIPTION OF THE PREFERRED EMBODIMENTS

FIG. 1 shows the constituent parts of the baby-soft wrist band 1. The foam strip 4 is wrapped around the wrist or ankle of the infant, the plasticized strip or label 2 is peeled off its backing strip 3 and wraps around the foam 4 and sticks onto itself. An easy way of applying the wrist band 1 is to partially peel the label 2 off its backing at a first end of the label 2, press the peeled off end onto the foam 4 at one end of the strip and wrap the foam 4 around the body part by means of the end of the label 2. Once the foam strip 4 surrounds the wrist or ankle the remaining backing strip 2 can be removed and label 2 adhered to the foam strip 2 by wrapping the whole of the foam strip 4 in the label 2. The second end of the label 2 then overlaps the first end of the label 2 and adheres the ends of the label 2 together. As can be seen from FIG. 1, the label 2 is longer than the foam strip 4 to ensure that the label 2 can stick down upon itself and completely surrounding the foam strip 4.

FIG. 1 also shows in broken lines an alternative embodiment wherein the two strips of material are of equal length.

Figure 2:

FIG. 2 shows the result of that operation, without the infant's body part being shown.

We claim:

1. A method of identifying a patient using a hospital style identification limb band, the limb band comprising two strips of material of unequal length to be joined together to form said limb band, wherein a first strip consists of an inert Latex free foam and a second strip consists of a plasticized strip in the form of an elongated label comprising an adhesive backing covered by a support layer and an area for printing information upon, wherein the area for printing information is printed with patient information, wherein the foam strip is sufficiently wider than the plasticised strip to avoid said plasticised strip coming into contact with a patient's skin and wherein said limb band is assembled by partially peeling the plasticised strip off the support layer to expose part of the adhesive backing, pressing said inert foam onto the exposed adhesive surface, wrapping said foam around the wrist or ankle of a person to be identified and wrapping the plasticised strip around the foam and overlapping it onto the other end of said plasticised strip itself, such that the ends of the plasticised strip are adhered to one another when wrapped around the wrist or ankle of the person, thus forming said wrist band securely and irremovably on the wrist or ankle of the person to be identified and wherein, said limb band cannot be reused after removal and any attempt at its removal will result in its destruction, since the adhesive is composed such that separation of the elongated plasticised strip from the foam causes tearing thereof.

\* \* \* \* \*